(12) United States Patent
Hallett et al.

(10) Patent No.: US 11,118,308 B2
(45) Date of Patent: *Sep. 14, 2021

(54) TREATMENT OF LIGNOCELLULOSIC BIOMASS WITH IONIC LIQUID

(71) Applicant: IP2IPO INNOVATIONS LIMITED, London (GB)

(72) Inventors: Jason P. Hallett, London (GB); Tom Welton, London (GB); Agnieszka Brandt, London (GB)

(73) Assignee: IP2IPO INNOVATIONS LIMITED, London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 15/946,486

(22) Filed: Apr. 5, 2018

(65) Prior Publication Data

US 2018/0327969 A1    Nov. 15, 2018

Related U.S. Application Data

(63) Continuation-in-part of application No. 14/776,415, filed as application No. PCT/GB2014/050824 on Mar. 14, 2014, now abandoned.

(30) Foreign Application Priority Data

Mar. 15, 2013  (GB) .................................. 1304872.3

(51) Int. Cl.
| | |
|---|---|
| *D21C 3/00* | (2006.01) |
| *C12P 19/02* | (2006.01) |
| *D21C 9/02* | (2006.01) |
| *C13K 1/02* | (2006.01) |
| *C12P 19/14* | (2006.01) |
| *D21C 3/04* | (2006.01) |
| *D21C 3/20* | (2006.01) |
| *D21C 1/04* | (2006.01) |
| *D21H 11/12* | (2006.01) |
| *D21C 5/00* | (2006.01) |
| *C13K 13/00* | (2006.01) |
| *D21C 11/00* | (2006.01) |

(52) U.S. Cl.
CPC .............. *D21C 3/003* (2013.01); *C12P 19/02* (2013.01); *C12P 19/14* (2013.01); *C13K 1/02* (2013.01); *C13K 13/002* (2013.01); *D21C 1/04* (2013.01); *D21C 3/04* (2013.01); *D21C 3/20* (2013.01); *D21C 5/00* (2013.01); *D21C 9/02* (2013.01); *D21C 11/0007* (2013.01); *D21H 11/12* (2013.01); *C12P 2201/00* (2013.01)

(58) Field of Classification Search
CPC ....................................................... C12P 19/14
See application file for complete search history.

(56) References Cited

U.S. PATENT DOCUMENTS

| 2,032,437 | A | 3/1936 | Richter |
|---|---|---|---|
| 3,598,695 | A | 8/1971 | Waterstradt |
| 4,462,865 | A | 7/1984 | Walles |
| 9,394,375 | B2 * | 7/2016 | Daly ......................... C08B 1/00 |
| 9,765,478 | B2 | 9/2017 | Brandt |
| 2007/0215300 | A1 | 9/2007 | Upfal |
| 2008/0164440 | A1 | 7/2008 | Maase |
| 2008/0185112 | A1 | 8/2008 | Argyropoulous |
| 2008/0190013 | A1 | 8/2008 | Argyropoulos |
| 2008/0190321 | A1 | 8/2008 | Maase et al. |
| 2008/0295980 | A1 | 12/2008 | Hallberg et al. |
| 2009/0234146 | A1 | 9/2009 | Cooney et al. |
| 2010/0006245 | A1 | 1/2010 | Myllymaki |
| 2010/0081798 | A1 | 4/2010 | Balensiefer et al. |
| 2010/0159521 | A1 | 6/2010 | Cirakovic et al. |
| 2010/0279372 | A1 | 11/2010 | Cho et al. |
| 2011/0073805 | A1 | 3/2011 | Dibble |
| 2011/0124056 | A1 | 5/2011 | Levie et al. |
| 2012/0010334 | A1 | 1/2012 | D'Andola |
| 2012/0245336 | A1 | 9/2012 | Daly et al. |
| 2012/0325421 | A1 | 12/2012 | Li et al. |
| 2013/0302854 | A1 | 11/2013 | Tabata |
| 2014/0005451 | A1 | 1/2014 | Mezza |
| 2014/0073016 | A1 | 3/2014 | Brandt |
| 2016/0040354 | A1 | 2/2016 | Hallett |

FOREIGN PATENT DOCUMENTS

| CN | 101298620 A | 11/2008 |
|---|---|---|
| CN | 101333777 A | 12/2008 |
| CN | 101787381 A | 7/2010 |
| CN | 103566904 A | 2/2014 |
| GB | 892744 | 3/1962 |
| IN | 2017/MUM/2008 A | 2/2009 |

(Continued)

OTHER PUBLICATIONS

International Search Report issued in co-pending International Application No. PCT/GB2014/050824, European Patent Office, dated Jun. 3, 2014, 5 pages.
Written Opinion issued in co-pending International Application No. PCT/GB2014/050824, European Patent Office, date Jun. 3, 2014, 6 pages.
"Determination of Structural Carbohydrates and Lignin in Biomass," NREL/TB-510-042618, National Renewable Energy Laboratory, Technical Report revised Aug. 2012, 18 pages.
"Preparation of Samples for Compositional Analysis," NREL/TP-510-42620, National Renewable Energy Laboratory, Technical Report dated Aug. 6, 2008, 12 pages.
"Determination of Total Solids in Biomass and Total Dissolved Solids in Liquid Process Samples," NREL/TP-510-42621, National Renewable Energy Laboratory, Technical Report issued Mar. 31, 2008, 9 pages.

(Continued)

*Primary Examiner* — Bin Shen
(74) *Attorney, Agent, or Firm* — McDonnell Boehnen Hulbert & Berghoff LLP

(57) ABSTRACT

The present disclosure relates to an improved method for treating a lignocellulose biomass in order to dissolve the lignin therein, while the cellulose does not dissolve. The cellulose pulp obtained can be used to produce glucose. In addition the lignin can be isolated for subsequent use in the renewable chemical industry.

19 Claims, 6 Drawing Sheets

(56) References Cited

FOREIGN PATENT DOCUMENTS

| WO | 90/11401 A1 | 10/1990 |
|---|---|---|
| WO | 98/49390 A1 | 11/1998 |
| WO | 2005/017001 A1 | 2/2005 |
| WO | 2005/017252 A1 | 2/2005 |
| WO | 2008073186 A2 | 6/2008 |
| WO | 2008/090155 A1 | 7/2008 |
| WO | 2008/090156 A1 | 7/2008 |
| WO | 2008/112291 A2 | 9/2008 |
| WO | 2009/105236 A1 | 8/2009 |
| WO | 2010/056790 A1 | 5/2010 |
| WO | 2012080702 A2 | 6/2012 |
| WO | 2012174459 A2 | 12/2012 |
| WO | 2014/0113884 A1 | 7/2014 |

OTHER PUBLICATIONS

"Enzymatic Saccharification of Lignocellulosic Biomass," NREL/TP-510-42619, National Renewable Energy Laboratory, Technical Report issued Mar. 21, 2008, 8 pages.

"Determination of Extractives in Biomass," NREL/TP-510-42619, National Renewable Energy Laboratory, Technical Report issued Jul. 17, 2005, 12 pages.

Copending U.S. Appl. No. 14/776,415, filed Sep. 14, 2015.

Brandt et al., "The effect of ionic liquid anion in the pretreatment of pine wood chips," Green Chemistry, 12, 672-79 (2010).

Fu et al., "Lignin extraction from straw by ionic liquids and enzymatic hydrolysis of the cellulosic residues," J. Agric. Food Chem., 58, 2915-22 (2010).

Lei et al., "Electrocoagulation Treatment of Chemithermomechanical Pulp (CTMP) Chemical Pretreatment Effluent," Bioinformatics and Biomedical Engineering (ICBBE), 2010 4th Int'l Conference ON, IEEE, Piscataway, NJ, USA, Jun. 18, 2010, pp. 1-4.

Lee et al., "Ionic Liquid-Mediated Selective Extraction of Lignin from Wood Leading to Enhanced Enzymatic Cellulose Hydrolysis," Biotechnology and Bioengineering, 102(5), 1368-76 (2009).

Hulsbosh, J. et al. "Biobased Ionic Liquids: Solvents for Green Processing Industry?" ACS Sustain Chem Eng. 2016, 4, 6, p. 2917-2931.

A. Brandt et al., "Ionic liquid pretreatment of lignocellulosic biomass with ionic liquid-water mixtures," Green Chem., 13, 2489-2499 (2011).

A. Brandt et al., "Deconstruction of lignocellulosic biomass with ionic liquids," Green Chem., 15, 550-583 (2013).

F.H. Isikgor and C.R. Becer, "Lignocellulosic biomass: a sustainable platform for the production of bio-based chemicals and polymers," Polym. Chem., 6, 4497-4559 (2015).

* cited by examiner

Different types of [alkylammonium][HSO$_4$] ionic liquids.

Different types of [alkylammonium][HSO$_4$] ionic liquids.

TREATMENT OF LIGNOCELLULOSIC BIOMASS WITH IONIC LIQUID

CROSS-REFERENCE TO RELATED APPLICATIONS

This application is a continuation-in-part of U.S. patent application Ser. No. 14/776,415, filed Sep. 14, 2015, now abandoned, which is a United States National Stage filing under 35 U.S.C. 371 of International Patent Application no. PCT/GB2014/050824, filed Mar. 14, 2014, which claims the benefit of priority of United Kingdom Patent Application no. GB 1304872.3, filed Mar. 15, 2013. Each of the above-referenced applications is hereby incorporated herein by reference in its entirety.

BACKGROUND OF THE DISCLOSURE

Field

The present invention relates to an improved method for treating a lignocellulose biomass in order to dissolve the lignin therein, while the cellulose does not dissolve. The cellulose pulp obtained can be used to produce glucose. In addition the lignin can be isolated for subsequent use in the renewable chemical industry as a source for aromatic platform chemicals.

Technical Background

Carbohydrates, such as sugars, can be used to produce a range of products that can be used as chemicals and solvents, for example the sugars can be fermented to make bioethanol. The lignin and hemicellulose can also be used to make a range of fuels and biochemicals. Currently biofuels are generally derived from food resources. This leads to several problems as there is competition with the food supply for the raw materials; the yield is low per unit area of land and a high energy input is required to grow the crops. It is possible to produce the sugar required by hydrolysing starch, or the sucrose produced by plants like sugar cane or sugar beet can be used. The problems could be alleviated if the woody part of plants from agricultural residues, forestry residues and energy crops could be used.

The woody or structural parts of the plant have evolved to withstand degradation. They are made up of mainly cellulose, hemicellulose and lignin. Pretreatment of the material is required in order to break up the structure. Generally pretreatment involves one or more of the following: removing the hemicelluose; modifying and solubilising the lignin; hydrolysing the hemicellulose-lignin linkages; and reducing the crystallinity of the cellulose fibres. This makes the cellulose more accessible to enzymes. Any potential inhibitors of the fermentation stage which are formed are removed during the conditioning stage.

Several pretreatment strategies have been previously described. These include steam explosion, catalysis with dilute acid or a base, ammonia fibre expansion, Organosolv pulping and biological pretreatment. All of these processes have their disadvantages. Pretreatment with ionic liquids has also been described. Ionic liquids (ILs) are salts that are liquid at the temperature of interest. The combination of anions and cations can be chosen to match the particular application required.

WO10/0056790 describes the use of substantially water free ILs to dissolve biomass which can then be separated using various solvents. WO08/090155 and WO08/090156 both describe the use of ILs to dissolve all the biomass components e.g. the lignin, hemicellulose and cellulose. In these methods the cellulose is separated from the other components usually by adding a suitable solvent so that the cellulose precipitates out and can be separated. Two recent reports applying ionic liquids containing [MeSO$_4$]$^-$ and diakylimidazolium cations for biomass pretreatment concluded that the ionic liquid is not capable of enhancing the digestibility of neither maple wood nor corn cob.

WO2008/112291 describes the use of ionic liquids to pretreat a lignin containing biomass to increase the yield in a subsequent saccharification reaction. The IL is used to swell the biomass structure including the cellulose, and not achieve any dissolution of the lignocellulose. Lignin can be recovered as a post-saccharification solid.

US2010-0081798 describes the use of ILs containing a polyatomic anion to solubilise lignocellulose. The cellulose dissolves in the IL.

WO2005/017252 discloses the use of ILs with an aromatic anion to dissolve the lignin from biomass allowing the cellulosic fibres obtained to be further processed.

WO 2005/017001 describes the use of ionic liquids such as 1-butyl-3-methylimidazolium chloride to dissolve lignocellulosic material using microwave irradiation and/or pressure. The lignin can be removed from the solution before the cellulose is precipitated. The ionic liquid dissolves both the lignin and cellulose material. The cation comprises a 5 or 6 membered heterocyclic ring optionally fused to a benzene ring.

WO2012/080702 describes the use of ILs to dissolve the lignin within a lignocellulose biomass, whilst the cellulose remains undissolved and unswelled. This allows the cellulose pulp produced to be mechanically separated before undergoing saccharification. The lignin can also be precipitated out from the IL by simply adding an anti-solvent, such as water. This means that the IL can be recycled.

Previous studies have used peralkylated or bulky aromatic cations, generally diakylimidazolium. These are expensive to use, and thus not suitable for commercial purposes. The cost of ionic liquids is one of the major deterrents for their use in biomass pretreatment and cellulose/lignin separation. Simple alkyl amines are manufactured on a bulk scale from simple precursors and are thus cheaper. Ionic liquids can be made from these alkyl amines by adding a suitable acid such as sulfuric acid, which is available at low cost.

SUMMARY OF THE DISCLOSURE

One aspect of the disclosure is method of treating a biomass to dissolve the lignin therein, but not the cellulose, the method comprising:

(a) contacting the lignocellulose biomass with a composition comprising an ionic liquid to produce a cellulose pulp, wherein the ionic liquid comprises
   (i) a cation of Formula I

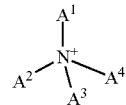

wherein A$^1$ to A$^4$ are each independently selected from H, an aliphatic, C$_{3-6}$ carbocycle, C$_{6-10}$ aryl, alkylaryl, and heteroaryl; and (ii) an anion selected from $C_{1-20}$ alkyl sulfate [AlkylSO$_4$]$^-$, $C_{1-20}$ alkylsulfonate [AlkylSO$_3$]$^-$, hydrogen sulfate [HSO$_4$]$^-$, hydrogen sulfite [HSO$_3$]$^-$, dihydrogen phosphate [H$_2$PO$_4$]$^-$, hydrogen phosphate [HPO$_4$]$^{2-}$ and acetate, [MeCO$_2$]$^-$, wherein if the anion is acetate then the composition further comprises 10-40% v/v water.

Another aspect of the disclosure is method of treating a biomass to dissolve the lignin therein, but not the cellulose, the method comprising:

(a) contacting the lignocellulose biomass with a composition comprising an ionic liquid to produce a cellulose pulp, wherein the ionic liquid comprises
(i) a cation of Formula I

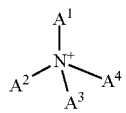

wherein $A^1$ to $A^4$ are each independently selected from H, an aliphatic, $C_{3-6}$ carbocycle, $C_{6-10}$ aryl, alkylaryl, and heteroaryl; and (ii) an anion selected from $C_{1-20}$ alkyl sulfate [AlkylSO$_4$]$^-$, $C_{1-20}$ alkylsulfonate [AlkylSO$_3$]$^-$, hydrogen sulfate [HSO$_4$]$^-$, hydrogen sulfite [HSO$_3$]$^-$, dihydrogen phosphate [H$_2$PO$_4$]$^-$, hydrogen phosphate [HPO$_4$]$^{2-}$, chloride and acetate, [MeCO$_2$]$^-$, wherein if the anion is acetate then the composition further comprises 10-40% v/v water.

Another aspect of the disclosure is a purified lignin made by a method as described herein.

Another aspect of the disclosure is a process of preparing glucose from a lignocellulose biomass comprising subjecting a cellulose pulp obtainable by a method as described herein to enzymatic hydrolysis.

DETAILED DESCRIPTION

Figure 1:
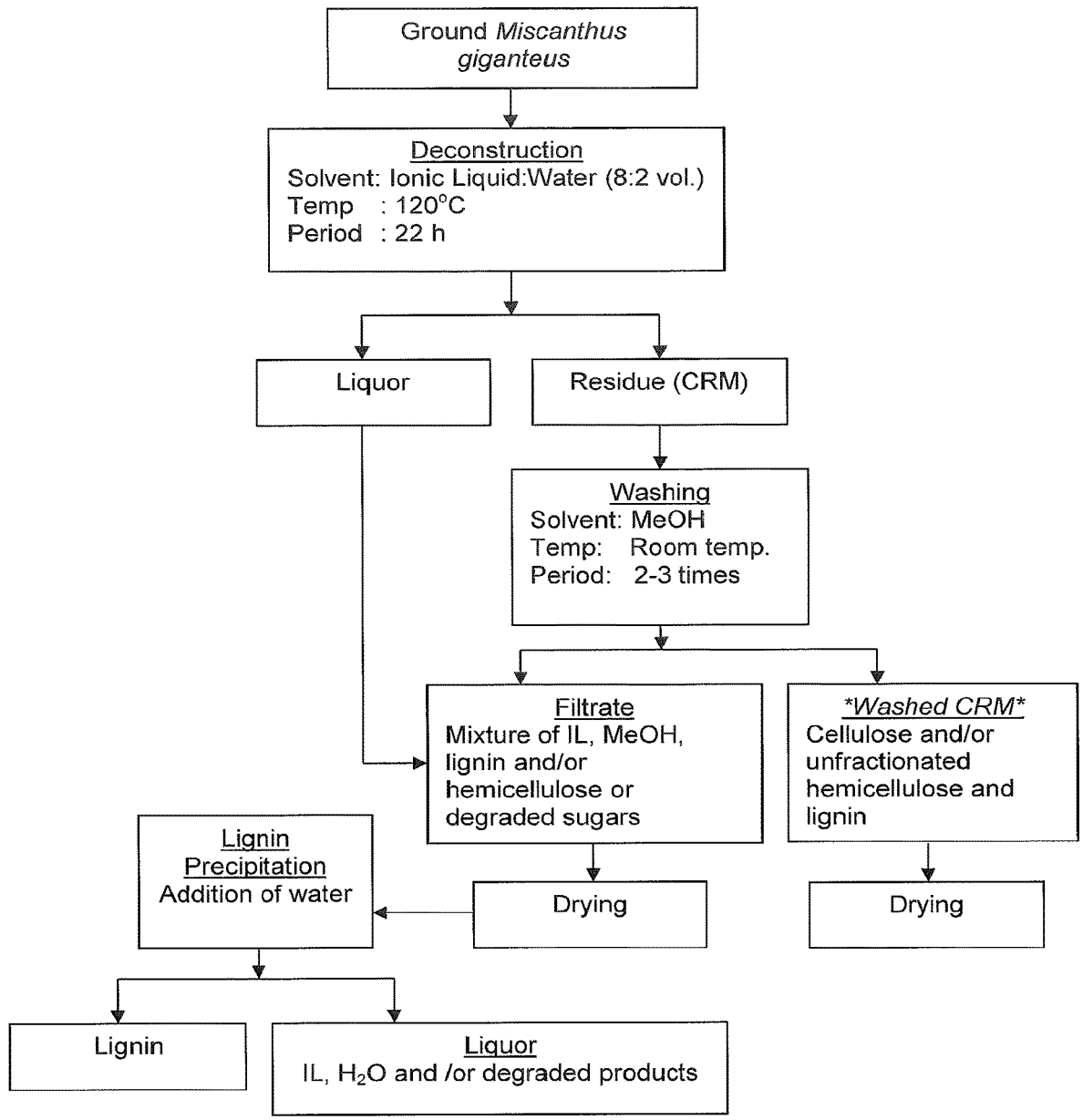
FIG. 1 outlines a process for the deconstruction of lignocellulose by ionic liquids. The washed carbohydrate rich material (CRM), can then be further processed to produce a range of products that can be used as fuels, chemicals and solvents, for example the sugars can be fermented to make bioethanol. The lignin obtained (bottom left side) can also be used to make a range of biochemicals or biofuels.

The present invention relates to a method of treating a lignocellulosic biomass to dissolve the lignin therein, but not the cellulose comprising:

(a) contacting the lignocellulose biomass with a composition comprising an ionic liquid to produce a cellulose pulp, wherein the ionic liquid comprises (i) a cation of Formula I

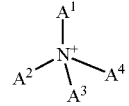

wherein
$A^1$ to $A^4$ are each independently selected from H, an aliphatic, $C_{3-6}$ carbocycle, $C_{6-10}$ aryl, alkylaryl, and heteroaryl; or a mixture thereof and
(ii) an anion or a mixture thereof selected from $C_{1-20}$ alkyl sulfate [Alkyl SO$_4$]$^-$, $C_{1-20}$ alkylsulfonate [Alkyl SO$_3$]$^-$, hydrogen sulfate [HSO$_4$]$^-$, hydrogen sulfite [HSO$_3$]$^-$, dihydrogen phosphate [H$_2$PO$_4$]$^-$, hydrogen phosphate [HPO$_4$]$^{2-}$ and acetate [MeCO$_2$]$^-$, wherein if the anion is acetate then the composition further comprises 10-40% v/v water. Preferably the anion is not acetate. In certain embodiments, chloride is also a suitable anion.

The IL is preferably heated with the biomass at 100-200° C., e.g., 100-180° C., preferably 120-140° C. The reaction is carried out for 1 min-24 hours, e.g., 15 min-24 hours, 1 min-23 hours, 15 min-23 hours, 1 min-22 hours, 15 min-22 hours, preferably 20 min-13 hours, more preferably 30 min-8 hours i.e. 45 min, 1 hr, 2 hr, 3 hr, 4 hr, 5 hr, 6 hr, 7 hr, 9 hr, 10 hr, 11 hr, 12 hr, 15 hr, 17 hrs, 20 hrs. Preferably the mixture is stirred, for example at 50-200 rpm.

As used herein the term "lignocellulosic biomass" refers to living or dead biological material that can be used in one or more of the disclosed processes. It can comprise any cellulosic or lignocellulosic material and includes materials comprising cellulose, and optionally further comprising hemicellulose, lignin, starch, oligosaccharides and/or monosaccharides, biopolymers, natural derivatives of biopolymers, their mixtures, and breakdown products. It can also comprise additional components, such as protein and/or lipid. The biomass can be derived from a single source, or it can comprise a mixture derived from more than one source. Some specific examples of biomass include, but are not limited to, bioenergy crops, agricultural residues, municipal solid waste, industrial solid waste, sludge from paper manufacture, yard waste, wood and forestry waste. Additional examples of biomass include, but are not limited to, corn grain, corn cobs, crop residues such as corn husks, corn stover, grasses including *Miscanthus×giganteus Miscanthus sinensis* and *Miscanthus sacchariflorus*, wheat, wheat straw, hay, rice straw, switchgrass, waste paper, sugar cane bagasse, sorghum, soy, components obtained from milling of grains, trees (e.g. pine), branches, roots, leaves, wood chips, wood pulp, sawdust, shrubs and bushes, vegetables, fruits, flowers, animal manure, multi-component feed, and crustacean biomass (i.e., chitinous biomass). It may be preferable to treat the biomass before use in the method of the invention. For example the biomass could be mechanically treated e.g. milling or shredding.

In a preferred embodiment the biomass is contacted with the ionic liquid composition prior to mechanical treatment. It has been found that treating the biomass, supplied as wood chips can reduce the energy required to grind the biomass. The IL composition appears to work as a lubricant during the grinding phase. The lignocellulosic biomass, supplied as wood chips, can be briefly impregnated with an IL composition at slightly elevated temperature (70-100° C., preferably 90° C.) before a mechanical size reduction step is applied. The IL composition can be contacted with the biomass for any length of time from several minutes to 18 hours or longer, preferably 5 minutes to 1 hour. This can be followed by further treatment with an ionic liquid composition as described herein to further solubilise the lignin content of the biomass.

As used herein "ionic liquid" refers to an ionized species (i.e. cations and anions). Typically they have a melting point below about 100° C. Any of the anions listed below can be used in combination with any of the cations listed below, to produce an ionic liquid for use in the invention.

The lignin in the lignocellulosic biomass is soluble in the ionic liquid at the treatment temperature, but the cellulose is not, so that a pulp comprising the cellulose is produced. Other components such as hemicellulose may preferably also dissolve in the ionic liquid.

The cation is an ammonium ion, a derivative thereof or a mixture thereof. These cations have the general formula

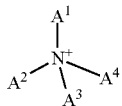

wherein
$A^1$ to $A^4$ are each independently selected from H, an aliphatic, $C_{3-6}$ carbocycle, $C_{6-10}$ aryl, alkylaryl, and heteroaryl. Preferably at least one of $A^1$ to $A^4$ is H. Preferably $A^1$ to $A^4$ are each independently selected from H, and an aliphatic. In one embodiment one of $A^1$ to $A^4$ is H, and the remaining three are each independently an aliphatic. Alternatively two of $A^1$ to $A^4$ are each H and the remaining two are each independently an aliphatic. Alternatively one of $A^1$ to $A^4$ is an aliphatic, and the remaining three are all H. Preferably the cation is not ammonium ($NH_4^+$.) i.e. at least one of $A^1$ to $A^4$ is not H.

The term "aliphatic" as used herein refers to a straight or branched chain hydrocarbon which is completely saturated or contains one or more units of unsaturation. Thus, aliphatic may be alkyl, alkenyl or alkynyl, preferably having 1 to 12 carbon atoms, preferably up to 6 carbon atoms or more preferably up to 4 carbon atoms. The aliphatic can have 1, 2, 3, 4, 5, 6, 7, 8, 9, 10, 11, or 12 carbon atoms.

The term "alkyl" as used herein, is typically a linear or branched alkyl group or moiety containing from 1 to 20 carbon atoms, such as 11, 12, 13, 14, 15, 16, 17, 18, or 19 carbon atoms. Preferably the alkyl group or moiety contains 1-10 carbon atoms i.e 2, 3, 4, 5, 6, 7, 8, 9, or 10 carbon atoms such as a $C_{1-4}$ alkyl or a $C_{1-6}$ alkyl group or moiety, for example methyl, ethyl, n-propyl, i-propyl, n-butyl, i-butyl and t-butyl, n-pentyl, methylbutyl, dimethylpropyl, n-hexyl, 2-methylpentyl, 3-methylpentyl, 2,3-dimethylbutyl, and 2,2-dimethylbutyl.

The term "alkenyl" as used herein, is typically a linear or branched alkenyl group or moiety containing from 2 to 20 carbon atoms, such as 11, 12, 13, 14, 15, 16, 17, 18, or 19 carbon atoms. Preferably the alkenyl group or moiety contains 2-10 carbon atoms i.e 2, 3, 4, 5, 6, 7, 8, 9, or 10 carbon atoms such as a $C_{2-4}$ alkenyl or a $C_{2-6}$ alkenyl group or moiety, for example ethenyl, 1-propenyl, 2-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, and 5-hexenyl.

The term "alkynyl" as used herein, is typically a linear or branched alkynyl group or moiety containing from 2 to 20 carbon atoms, such as 11, 12, 13, 14, 15, 16, 17, 18, or 19 carbon atoms. Preferably the alkynyl group or moiety contains 2-10 carbon atoms i.e 2, 3, 4, 5, 6, 7, 8, 9, or 10 carbon atoms such as a $C_{2-4}$ alkynyl or a $C_{2-6}$ alkynyl group or moiety, for example ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, and 5-hexynyl.

The term "carbocycle" as used herein refers to a saturated or partially unsaturated cyclic group having 3 to 6 ring carbon atoms, i.e. 3, 4, 5, or 6 carbon atoms. A carbocycle is preferably a "cycloalkyl", which as used herein refers to a fully saturated hydrocarbon cyclic group. Preferably, a cycloalkyl group is a $C_3$-$C_6$ cycloalkyl group.

The term "$C_{6-10}$ aryl group" used herein means an aryl group constituted by 6, 7, 8, 9 or 10 carbon atoms and includes condensed ring groups such as monocyclic ring group, or bicyclic ring group and the like. Specifically, examples of "$C_{6-10}$ aryl group" include phenyl group, indenyl group, naphthyl group or azulenyl group and the like. It should be noted that condensed rings such as indan and tetrahydro naphthalene are also included in the aryl group.

The terms "alkylaryl" as used herein refers to an alkyl group as defined below substituted with an aryl as defined above. The alkyl component of an "alkylaryl" group may be substituted with any one or more of the substituents listed above for an aliphatic group and the aryl or heteroaryl component of an "alkylaryl" or "alkylheteroaryl" group may be substituted with any one or more of the substituents listed above for aryl, and carbocycle groups. Preferably, alkylaryl is benzyl.

The term "heteroaryl" as used herein refers to a monocyclic or bicyclic aromatic ring system having from 5 to 10 ring atoms, i.e. 5, 6, 7, 8, 9, or 10 ring atoms, at least one ring atom being a heteroatom selected from O, N or S.

An aliphatic, aryl, heteroaryl, or carbocycle group as referred to herein may be unsubstituted or may be substituted by one or more substituents independently selected from the group consisting of halo, $C_{1-6}$ alkyl, $-NH_2$, $-NO_2$, $-SO_3H$, $-OH$, alkoxy, $-COOH$, or $-CN$.

The term "halogen atom" or "halo" used herein means a fluorine atom, a chlorine atom, a bromine atom, an iodine atom and the like, preferably a fluorine atom or a chlorine atom, and more preferably a fluorine atom.

The ionic liquid may contain one of the listed cations, or a mixture thereof.

Preferably the cation is an alkylammonium or a mixture thereof. Optionally one or more of the alkyl groups may be substituted with $-OH$ to form an alkanolammonium, which can also be referred to as an alcoholammonium. As used herein an "alkylammonium" includes trialkylammoniums, dialkylammoniums, monoalkylammoniums, and alcoholammoniums including trialcoholammoniums, dialcoholammoniums and monoalcoholammonium. Trialkylammoniums include trimethylammonium, triethylammonium, and triethanolammonium. Examples of dialkylammoniums include diethylammonium, diisopropylammonium, and diethanolammonium. Monoalkylammoniums include methylammonium, ethylammonium, and monoethanolammonium. In other embodiments, N,N-dimethylbutylammonium is also a suitable trialkylammonium.

Another preferred cation is diethylbenzylammonium.

The anion is selected from $C_{1-20}$ alkyl sulfate [Alkyl $SO_4$]$^-$, $C_{1-20}$ alkylsulfonate [Alkyl $SO_3$]$^-$, hydrogen sulfate [$HSO_4$]$^-$, hydrogen sulfite [$HSO_3$]$^-$, dihydrogen phosphate [$H_2PO_4$]$^-$, hydrogen phosphate [$HPO_4$]$^{2-}$ and acetate [$MeCO_2$]$^-$ or a mixture thereof, with the proviso that if the anion is acetate then the composition comprises 10-40% v/v water. Preferably the anion is selected from methyl sulfate [$MeSO_4$]$^-$, hydrogen sulfate [$HSO_4$]$^-$, methanesulfonate [$MeSO_3$]$^-$, and acetate [$MeCO_2$]$^-$. In certain embodiments, chloride is also a suitable anion.

Preferred ionic liquids for use in the invention are [alkylammonium][$HSO_4$], for example triethylammonium hydrogen sulfate [$Ethyl_3NH$][$HSO_4$], diethylammonium hydrogen sulfate [$Ethyl_2NH_2$][$HSO_4$], and ethylammonium hydrogen sulfate [$EthylNH_3$][$HSO_4$]

Ionic liquids can be prepared by methods known to the person skilled in the art or obtained commercially.

It has been surprisingly found that the yield in the saccharification step can be improved if the pretreatment composition comprises water. Therefore in one preferred embodiment the composition comprises the IL and 5-40% v/v water. Preferably the composition comprises 20-30% v/v water preferably 10-20% v/v.

It has also been discovered that the presence of an excess of acid accelerates the pretreatment resulting in improved lignin removal and thus enhanced saccharification yields, as lignin interferes with the enzyme binding. Thus, the glucose yield is improved. Therefore in one preferred embodiment the composition further comprises 0.01-20% v/v acid, preferably 1-5% v/v acid. The addition of a small amount of acid significantly accelerates the pre-treatment process, when other variables such as water content and temperature are kept constant. The acid can be selected from any known strong acid such as hydrochloric acid, sulfuric acid, nitric acid, phosphoric acid hydroiodic acid, perchloric acid and hydrobromic acid. Preferably the acid is sulfuric or phosphoric acid.

The ionic liquids of the present invention dissolve the lignin within the biomass but they do not dissolve the cellulose. The majority of cellulose remains solid, preferably at least 90%, more preferably 95%. The majority of the cellulose remains unswelled, preferably at least 90%, more preferably 95%, even more preferably 99%. Swelling can be measured by methods well known to those skilled in the art. One such method is measuring the fibre diameters and lengths before and after treatment using an optical microscope or SEM, or by powder diffraction. The solid cellulose can be easily removed from the liquid phase mechanically, for example by filtration. The separated pulp can then be washed and used in the saccharification process. This removes the need for a separate precipitation step to obtain the cellulose once the biomass has been treated. Thus in a preferred embodiment the method of the invention further comprises the step of separating the ionic liquid from the pulp produced. It has been surprisingly found that the solubility of the lignin is higher in ILs containing an alkylammonium cation as compared to an imidazolium based cation. For example, the lignin yield obtained was higher for triethylammonium sulfate[$HNEt_3$][$HSO_4$] in comparison to 1-butylimidazole hydrogen sulfate [$C_4Him$][$HSO_4$]—30 weight % vs. 25 weight % at 90° C.

In a preferred embodiment the pulp is washed with water or an organic solvent miscible with the ionic liquid. The separation efficiency and the ionic liquid recovery can be enhanced by washing the pulp with water or an organic solvent that is miscible with the ionic liquid. The water or organic solvent is removed before or potentially after the lignin is precipitated. Examples of suitable organic solvents include aliphatic alcohols such as methanol and ethanol.

It is possible to precipitate out the lignin dissolved in the IL compositions. Therefore in another preferred embodiment the method further comprises (c) adding an anti-solvent to the ionic liquid which has been separated from the pulp, to precipitate out the dissolved lignin; and (d) separating the precipitated solid from the anti-solvent/ionic liquid.

As used herein an "anti-solvent" is a liquid which causes the lignin to precipitate out from the ionic liquid containing the solubilised lignin produced in step (a). Generally an 'antisolvent' is a solvent in which lignin is insoluble. The anti-solvent is preferably water. The ionic liquid can be recovered by removing the anti-solvent, for example by evaporation. The resulting ionic liquid can then be recycled to be used again in the method. Thus in another embodiment the method further comprises (e) removing the anti-solvent from the ionic liquid obtained in (d). As the presence of some water during step (a) improves the yield, less energy is required to dry the IL.

The cellulose pulp obtained from the method of the invention can be used to undergo saccharification to obtain glucose. This can then be used in the fermentation process to obtain biofuel and biochemicals. Thus in a second aspect the invention provides a process of preparing glucose from a lignocellulose biomass comprising subjecting a cellulose pulp obtainable by suitable methods of the invention to enzymatic hydrolysis. In a further aspect the invention provides glucose obtained by this hydrolysis.

Suitable enzymes for use in the process include commercially available preparations of cellulases such as *T. reseei* cellulase and Novozyme 188 cellobiase that also contains hemicellulolytic activity. Other useful enzymes include esterases, either acetyl esterases or feruloyl esterases, which cleave substituents that are esterified to hemicellulose. The process is preferably carried out in an aqueous medium at a suitable pH for the enzymes. The conditions can be optimised in relation to pH, temperature and the medium used depending on the enzyme mixture required. Such methods are well known to the skilled person. The process is preferably carried out in accordance with "Enzymatic saccharification of lignocellulosic biomass" (NREL/TP-510-42629), issue date Mar. 21, 2008

In a further aspect the invention relates to lignin obtained by suitable methods as described herein.

The invention will now be described in the following non-limiting examples with reference to the figures described above.

EXAMPLES

Example 1

Synthesis of [HNR$_3$][HSO$_4$] Ionic Liquids 95 wt. % (2.5 moles, 245 g) H$_2$SO$_4$ was dissolved in distilled water (200 ml), resulting in a 12M solution of H$_2$SO$_4$. This solution was added dropwise to the amine (i.e., 2.5 moles, 252.5 g of triethylamine) over the course of 1 hr. This process was conducted in an ice bath to maintain low temperature. After warming to room temperature the mixture was stirred vigorously overnight. Excess water was removed from the ionic liquid by rotary evaporator and subsequently dried in vacuo overnight.

Deconstruction of biomass in [HNR$_3$][HSO$_4$] Ionic Liquids.

A flow chart of the deconstruction process is summarized in FIG. 1. *Miscanthus giganteus* (1.0 g oven-dried basis) with particle sizes of 180-850 μm was loaded into a culture vial. [HNR$_3$][HSO4] ionic liquid (8 ml) and distilled water (2 ml) were added, giving a total volume of 10 ml. The vial was screwed tightly, placed in an oven and incubated at 120° C. for 22 h. After the incubation was completed, the mixture was filtered, giving carbohydrate rich material (CRM) and liquor. The CRM was washed with methanol (MeOH) three times and then dried at room temperature for a few days. The filtrates were collected and combined with the liquor. The combined solution was then dried to evaporate MeOH, yielding concentrated liquor. Water was then added into the concentrated liquor, precipitating the lignin. The CRM was kept for the enzymatic saccharification assay. The precipitated lignin was dried at room temperature. The process was repeated for the deconstruction in other ionic liquids.

Saccharification

Enzymatic saccharification was performed according to LAP "Enzymatic saccharification of lignocellulosic biomass" (NREL/TP-510-42629), issue date Mar. 21, 2008. The enzymes were *T. reseei* cellulase and Novozyme 188 cellobiase that also contains hemicellulolytic activity and can therefore hydrolyse xylan (both from Sigma-Aldrich). Glucose and hemicellulose yields were calculated based on the glucose and hemicellulose content of the untreated biomass, respectively.

Example 2

The influence of the number of hydrogen atoms present on the ammonium ion were compared. Ionic liquids wherein the cation contained 1, 2, or 3 ethyl groups were prepared and performance compared as shown in Table 1. The pulp recovery refers to the total carbohydrates recovered in the solid. The percentage (%) solubilised refers to the percentage of the biomass which dissolved in the ionic liquid.

Figure 2:
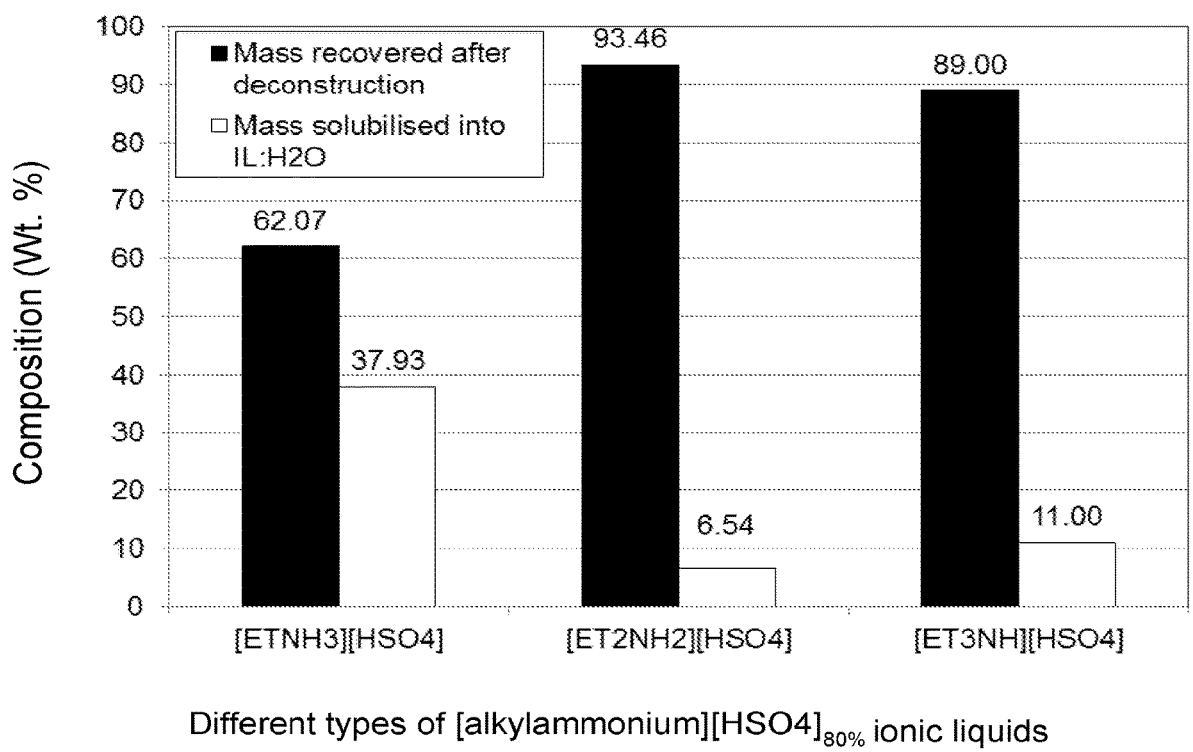
FIG. 2 show the deconstruction of *Miscanthus* in [R$_x$NH$_y$][HSO$_4$]$_{80\%}$

FIG. 2 shows a comparison of the deconstruction of *Miscanthus* in various alkylammoniums, [R$_x$NH$_y$][HSO$_4$]$_{80\%}$ wherein R is ethyl, x is 1-3 and y is 1-3.

The treatment was carried out at 120° C. for 22 h. For [NH4][HSO4], the mass recovered was more than 200%. Ammonium bisulfate ([NH4][HSO4]) is a salt as opposed to an ionic liquid. The salt crystallised on the pulp, so that the measured yield is extremely high due to solid solvent contamination. The alkylammonium hydrogen sulfates tested were ionic liquids. The pulp recovery improves as the number of alkyl groups increase in the cation used in the ionic liquid.

The activity of the ionic liquids was compared by carrying out a short saccharification reaction. The reaction was not run longer otherwise the yields could be too high to be able to make a meaningful comparison between the different cations.

Figure 3:
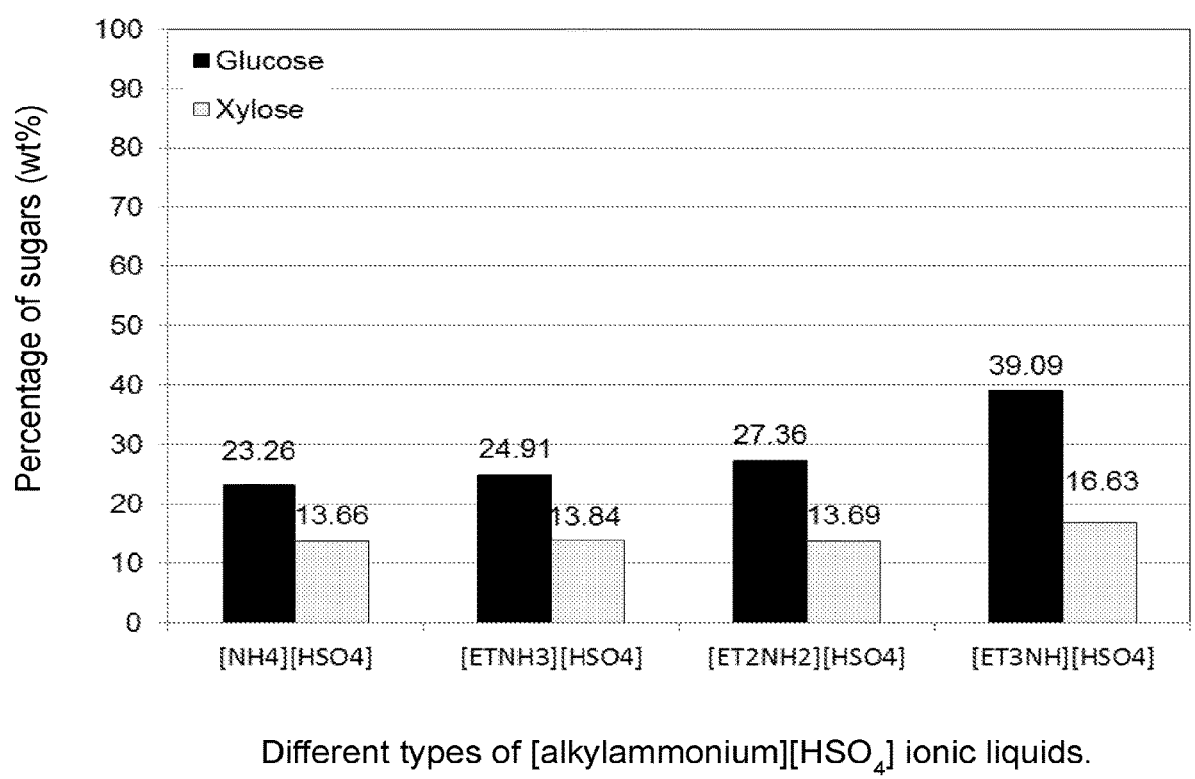
FIG. 3 shows the results of an enzymatic saccharification assay at 50° C. for 72 Hours as a percentage of the sugars based on 0.1 g of recovered CRM after the ionic liquid treatment process.
Figure 4:
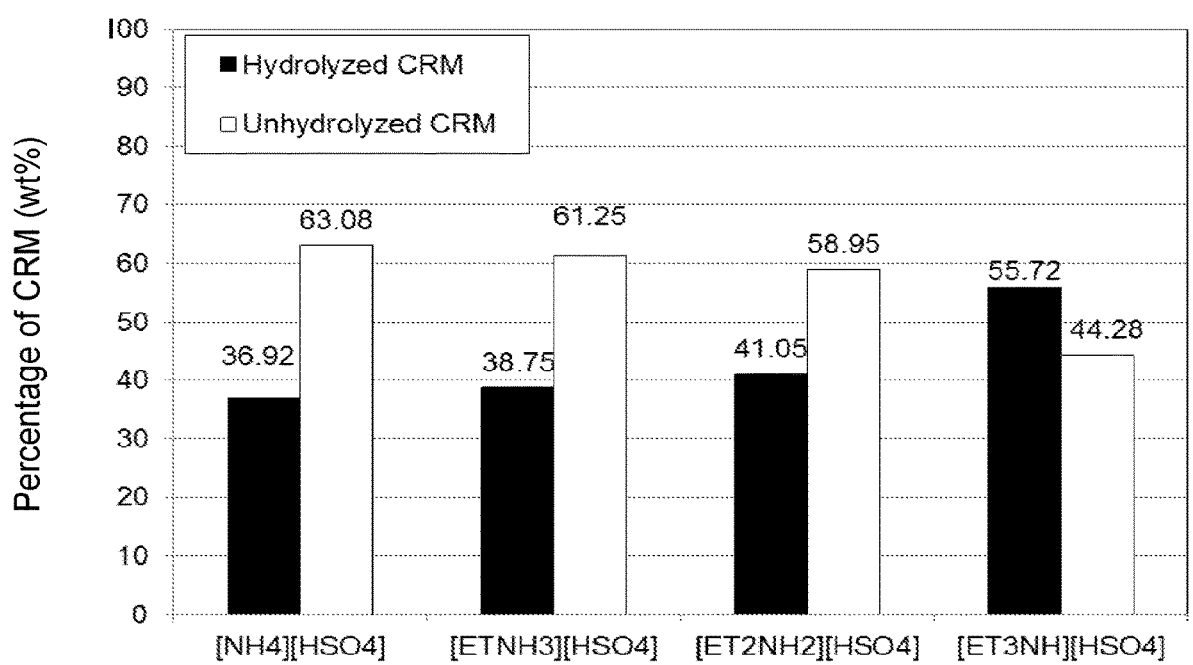
FIG. 4 shows the results of an enzymatic saccharification assay at 50° C. for 72 Hours as a percentage of the CRM based on 0.1 g of recovered CRM after the ionic liquid treatment process.

FIG. 3 shows the results of the enzymatic saccharification assay at 50° C. for 72 Hours as a percentage of the sugars. FIG. 4 shows the results of the enzymatic saccharification assay at 50° C. for 72 Hours as a percentage of the CRM.

The sugar yields (both glucose and xylose as shown as the percentage of cellulose or hemicellulose converted in the columns marked Y in Table 1) are highest for the

TABLE 1

1 g of miscanthus contains 43.6% of cellulose and 24.3% of hemicellulose

| | Biomass used (g) | Pulp recovery (%) | Solubilized into IL:H2O (%) | Biomass hydrolyzed to glucose (%) (X) | Cellulose conversion (%) (Y) | Biomass hydrolyzed to xylose (%) (X) |
|---|---|---|---|---|---|---|
| [NH$_4$][HSO$_4$] | 1 | 200 | — | 10.13 | 23.25 | 3.31 |
| [H$_3$NEt][HSO$_4$] | 1 | 62.07 | 37.93 | 10.86 | 24.91 | 3.36 |
| [H$_2$NEt$_2$][HSO$_4$] | 1 | 93.46 | 6.54 | 11.92 | 27.36 | 3.32 |
| [HNEt$_3$][HSO$_4$] | 1 | 89.00 | 11.00 | 17.04 | 39.08 | 4.04 |

1 g of miscanthus contains 43.6% of cellulose and 24.3% of hemicellulose

| | Hemicellulose conversion (%) (Y) | Total hydrolyzed (%) | Unhydrolyzed cellulose (%) (X") | Unhydrolyzed hemicelluloses (%) (X") | Total Unhydrolyzed cellulose and hemicellulose (%) |
|---|---|---|---|---|---|
| [NH$_4$][HSO$_4$] | 13.66 | 13.44 | 33.47 | 20.99 | 54.46 |
| [H$_3$NEt][HSO$_4$] | 13.83 | 14.22 | 32.74 | 20.94 | 53.68 |

TABLE 1-continued

| | | | | | |
|---|---|---|---|---|---|
| [H2NEt2][HSO4] | 13.69 | 15.24 | 31.68 | 20.98 | 52.66 |
| [HNEt3][HSO4] | 16.63 | 21.08 | 26.56 | 20.26 | 46.82 |

X = For example for [NH4][HSO4], only 10.13% of the biomass was hydrolyzed to glucose.
X" = For example for [NH4][HSO4], after treatment 33.47% of the biomass was unhydrolyzed cellulose.
Y = For example for [NH4][HSO4], 23.25% conversion refers to: = (10.13% hydrolyzed cellulose/43.6% (cellulose in mischantus) × 100 = 23.25%
1. Saccharification yield relative to untreated whole lignocelluloses (X).
2. Yield relative to the theoretical possible e.g. % glucose obtained from the 43.6% cellulose that was contained in Miscanthus prior to treatment (Y).
3. Amount of cellulose not recovered by enzymatic saccharification relative to total amount in whole untreated biomass (X").
4. Amount of hemicellulose not recovered by enzymatic saccharification on relative to total amounts in whole untreated biomass (X").

HNEt3], with the [H2NEt2] being close. However, [H2NEt2] dissolves more hemicellulose and/or lignin. [H3NEt] dissolves even more hemicellulose and lignin, and has a lower percentage conversion of glucose. Thus under the same reaction conditions, the saccharification yields increase, as measured by the "Total hydrolysed" in Table 1, when a cation with more alkyl groups is used in the ionic liquid.

Example 3

1. Biomass Pretreatment:

8 g Dried triethylammonium hydrogen sulfate (1:1 mol/mol acid:base ratio) and 2 g water (minus amount of moisture introduced by biomass) was added into 15 ml ACE pressure tubes with Teflon cap and silicone O-ring and mixed, then the air-dried Miscanthus×gigantheus (whole stems, ground and sieved, 180-850 μm particle size range) was added. The vial was capped tightly and placed in an oven for 24 hours at 120° C. All experiments were performed in triplicate.

2. Fractionation

The ACE vial was allowed to cool down to room temperature (RT). 40 ml absolute ethanol was added and the suspension transferred into a 50 ml plastic centrifugation tube. The tube was left at RT for 1 h and centrifuged for 50 minutes at maximum speed. The solid was separated from the lignin containing ionic liquid-ethanol-solution by careful decanting. The liquid was collected in a clean 250 ml round bottom flask with stir bar. 40 ml fresh ethanol was added and the washing and separation repeated 3 more times. The pulp was transferred into cellulose thimbles and Soxhlet extracted with 150 ml absolute ethanol for 20 h in total. The combined ethanol ionic liquid washes were dried with the rotavap or the parallel evaporator at 40° C. until the IL was solidified.

The wet pulp was dried in the thimble overnight. Once dry, the pulp was transferred from the thimble onto a piece of tared aluminium foil on an analytical balance, the air-dried weight recorded and the pulp stored in labelled a plastic bag. The moisture content of the pulp was determined to calculate the oven-dried yield.

3. Lignin Precipitation and Wash:

The dried IL liquor was mixed with distilled water (1 g of IL:3 ml of distilled water) and left for at least 1 h, then transferred into a 50 ml centrifugation tube and centrifuged for 40 minutes. The lignin was separated from the solution by decanting. The precipitate was washed by adding distilled water (same amount as for precipitation, 1 g of IL: 3 ml of distilled water), followed by centrifugation for 40 minutes and decanting (2× repeats of washing the lignin pellet). After the third decanting, the lignin was dried using a vacuum oven at 45° C. and the yield determined.

Enzymatic Saccharification

The air-dried pulps were subjected to enzymatic saccharification following the LAP procedure "Enzymatic Saccharification of Lignocellulosic Biomass" (NREL/TP-510-42629). The enzymes were T. reseei cellulase and Novozyme 188 cellobiase that also contains hemicellulolytic activity and can therefore hydrolyse xylan (both from Sigma-Aldrich)

Compositional Analysis

The glucan, hemicellulose and lignin content of untreated Miscanthus was determined was carried out following the LAP procedures "Preparation of samples for compositional analysis" (NREL/TP-510-42620) and "Determination of Structural Carbohydrates and Lignin in Biomass" (NREL/TP-510-42618). The extractives in untreated Miscanthus giganteus were removed and quantified according to the LAP "Determination of extractives in biomass" (NREL/TP-510-42619).

The oven-dry weight (ODW) of lignocellulose biomass was determined according to the procedure described in the LAP "Determination of Total Solids in Biomass and Total Dissolved Solids in Liquid Process Samples" (NREL/TP-510-42621).

Table 2 shows the fractionation yields after pretreatment of Miscanthus with 80% triethylammonium hydrogen sulfate 20 wt % water mixtures (1:1 acid base ratio) at 120° C. for 24 h. The wash solvent used to separate the pulp from the IL/lignin was ethanol. Also shown are the glucose and xylose yields after 7 days enzymatic saccharification of the pulp fraction. The lignin content was 24.5%, the xylose content 24.3% and the glucan content of untreated biomass 47.7%. It is shown that the lignin yield is higher than seen with alkylimidazolium salts, while saccharification yields are good.

| | | Yield (wt % of untreated biomass) | % of theoretical possible |
|---|---|---|---|
| Fractionation | Pulp yield | 51.8 | n/a |
| | Lignin precipitate yield | 20.6 | 84.1 |
| | Dissolved into liquor | 27.6 | |
| Saccharification of pulp | Glucose | 28.5 | 59.8 |
| | Xylose | 4.5 | 18.5 |

Figure 5:
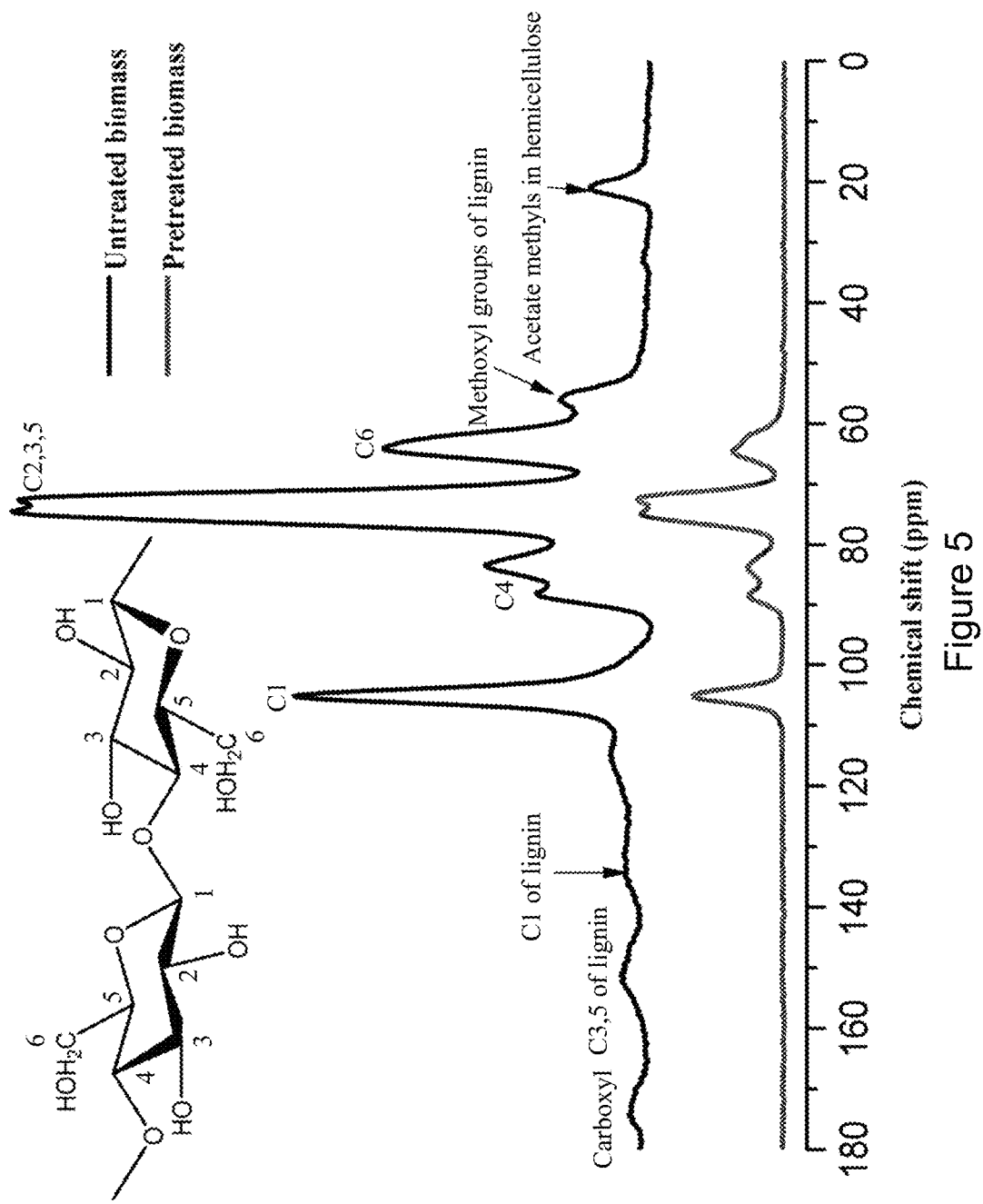
FIG. 5 shows $^{13}$C cross polarization, magic-angle spinning (CP-MAS) NMR spectrum for untreated *Miscanthus giganteus* and *Miscanthus* pretreated with 80 wt % triethylammonium hydrogen sulfate in 20 wt % water mixtures at 120° C. The figure shows that the peaks belonging to lignin and hemicellulose of the untreated samples disappeared, suggesting lignin and hemicellulose were removed after the pretreatment process.

FIG. 5 shows $^{13}C$ cross polarization, magic-angle spinning (CP-MAS) NMR spectrum for untreated Miscanthus giganteus and Miscanthus pretreated with 80 wt % triethylammonium hydrogen sulfate in 20 wt % water mixtures at 120° C. The figure shows that the peaks belonging to lignin and hemicellulose of the untreated samples disappeared, suggesting lignin and hemicellulose was removed after the pretreatment process.

Figure 6:
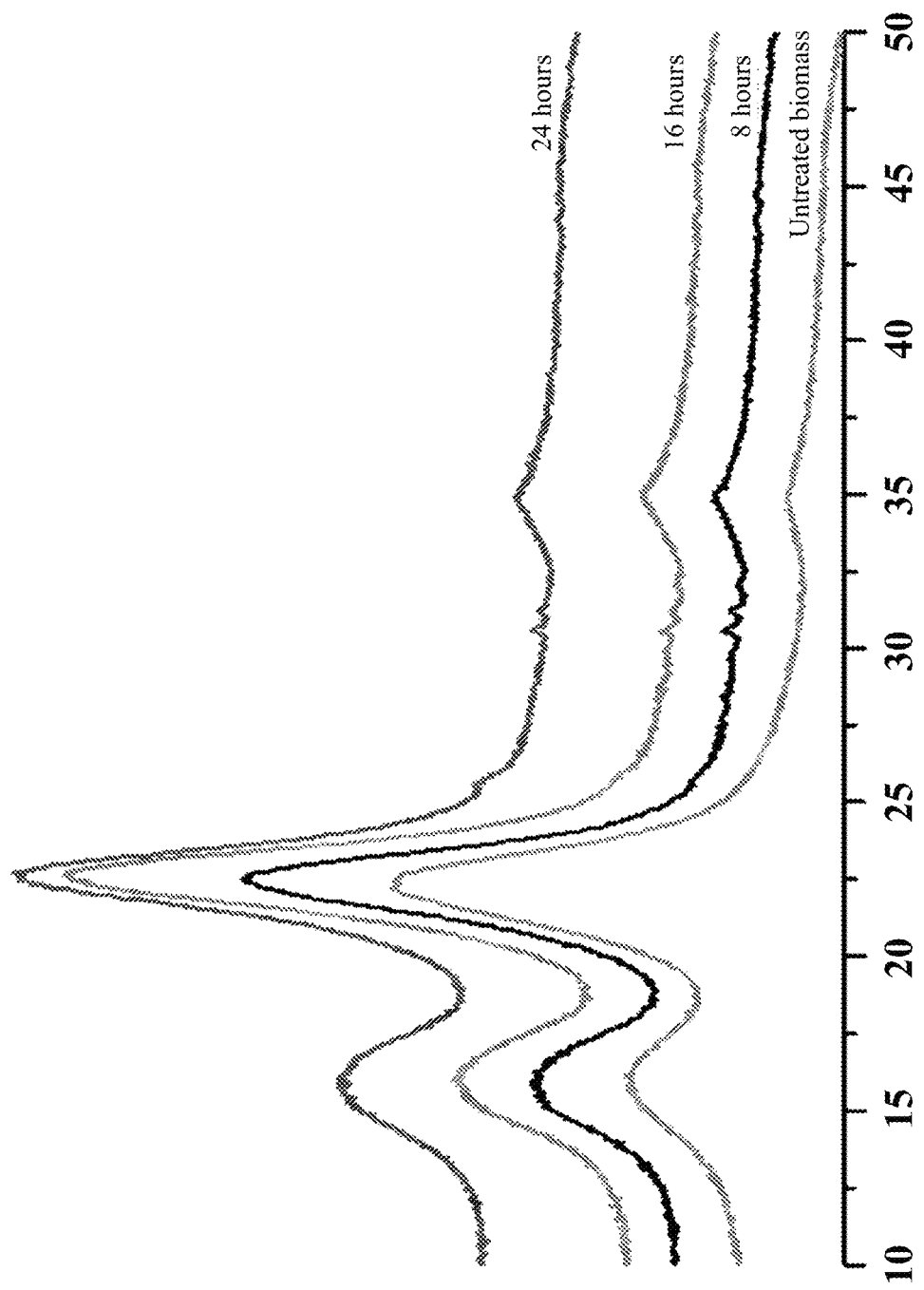
FIG. 6 shows the X-ray diffractograms of *Miscanthus giganteus*, untreated and the resulting pulp after treatment with 80 wt % triethylammonium hydrogen sulfate 20 wt % water mixtures for 8, 16, 24 hours. There is no evidence for transformation of the native cellulose crystalline I structure into cellulose II, which is observed if cellulose is swollen or dissolved.

FIG. 6 shows the X-ray diffractograms of *Miscanthus giganteus*, untreated and the resulting pulp after treatment with 80 wt % triethylammonium hydrogen sulfate 20 wt % water mixtures for 8, 16, 24 hours. There is no evidence for transformation of the native cellulose crystalline I structure into cellulose II, which is observed if cellulose is swollen or dissolved.

What is claimed is:

1. A method of treating a biomass containing lignin and cellulose, the method comprising:
   (a) dissolving lignin of the biomass by contacting the lignocellulose biomass with a composition comprising an ionic liquid while leaving cellulose of the biomass undissolved to produce a cellulose pulp, wherein the ionic liquid comprises
      (i) a cation of Formula I

wherein $A^1$ to $A^4$ are each independently selected from the group consisting of H, an aliphatic, $C_{3-6}$ carbocycle, $C_{6-10}$ aryl, alkylaryl, and heteroaryl; and
      (ii) an anion selected from the group consisting of $C_{1-20}$ alkyl sulfate [AlkylSO$_4$]$^-$, $C_{1-20}$ alkylsulfonate [AlkylSO$_3$]$^-$, hydrogen sulfate [HSO$_4$]$^-$, hydrogen sulfite [HSO$_3$]$^-$, dihydrogen phosphate [H$_2$PO$_4$]$^-$, hydrogen phosphate [HPO$_4$]$^{2-}$ and acetate [MeCO$_2$]$^-$, wherein if the anion is acetate then the composition further comprises 10-40% v/v water and if the anion is not acetate then the composition comprises 5-40% v/v water.

2. A method as claimed in claim 1 wherein at least one of $A^1$ to $A^4$ is not H.

3. A method as claimed in claim 1 wherein at least one of $A^1$ to $A^4$ is H.

4. A method as claimed in claim 1 wherein said cation is an alkylammonium or mixture thereof.

5. A method as claimed in claim 1 wherein said cation is an alcoholammonium or mixture thereof.

6. A method as claimed in claim 1 wherein the anion is selected from the group consisting of [MeSO$_4$]$^-$, acetate, [HSO$_4$]$^-$ and [MeSO$_3$]$^-$.

7. A method as claimed in claim 1 wherein the cation is selected from the group consisting of trimethylammonium, triethylammonium, triethanolammonium, diethylammonium, diisopropylammonium, diethanolammonium, methylammonium, ethylammonium, monoethanolammonium, and diethylbenzylammonium.

8. A method as claimed in claim 1 wherein the ionic liquid is alkylammonium hydrogen sulfate.

9. A method as claimed in claim 1 wherein the ionic liquid is triethylammonium hydrogen sulfate [HSO$_4$]$^-$, diethylammonium hydrogen sulfate [HSO$_4$]$^-$, or ethylammonium hydrogen sulfate [HSO$_4$]$^-$.

10. A method as claimed in claim 1 wherein the anion is not acetate and the composition comprises 5-40% v/v water.

11. A method as claimed in claim 1 wherein the ionic liquid further comprises 0.01-20% v/v acid.

12. A method as claimed in claim 1 wherein the lignocellulose biomass is contacted with the composition at 100-180° C.

13. A method as claimed in claim 1 wherein the lignocellulose biomass is contacted with the composition for 15 min-24 hours.

14. A method as claimed in claim 1 further comprising
   (b) separating the ionic liquid from the pulp produced in (a).

15. A method as claimed in claim 14 further comprising
   (c) adding an anti-solvent to the ionic liquid obtained in (b) to precipitate out the dissolved lignin;
   (d) separating the precipitated solid from the anti-solvent/ionic liquid; and
   (e) removing the anti-solvent from the ionic liquid obtained in (d),
   wherein the anti-solvent is water.

16. A method as claimed in claim 1 wherein the biomass is contacted with the composition prior to mechanical processing.

17. A method as claimed in claim 1 wherein the biomass is contacted with the composition after mechanical processing.

18. A method as claimed in claim 1 further comprising the step of washing the pulp with water or an organic solvent which is miscible with the ionic liquid.

19. A method as claimed in claim 1 wherein at least one of $A^1$ to $A^4$ is not H, and at least one of $A^1$ to $A^4$ is H.

* * * * *